US009885709B2

(12) United States Patent
Bergmann et al.

(10) Patent No.: US 9,885,709 B2
(45) Date of Patent: *Feb. 6, 2018

(54) DETERMINATION OF A MIDREGIONAL PROADRENOMEDULLIN PARTIAL PEPTIDE IN BIOLOGICAL FLUIDS FOR DIAGNOSTIC PURPOSES, AND IMMUNOASSAYS FOR CARRYING OUT SUCH A DETERMINATION

(75) Inventors: Andreas Bergmann, Berlin (DE); Joachim Struck, Berlin (DE)

(73) Assignee: B.R.A.H.M.S. GMBH, Henningsdorf (GR)

( * ) Notice: Subject to any disclaimer, the term of this patent is extended or adjusted under 35 U.S.C. 154(b) by 1094 days.

This patent is subject to a terminal disclaimer.

(21) Appl. No.: 10/551,298

(22) PCT Filed: Jan. 29, 2004

(86) PCT No.: PCT/EP2004/000806
§ 371 (c)(1),
(2), (4) Date: Sep. 23, 2005

(87) PCT Pub. No.: WO2004/090546
PCT Pub. Date: Oct. 21, 2004

(65) Prior Publication Data
US 2007/0212742 A1    Sep. 13, 2007

(30) Foreign Application Priority Data

Apr. 10, 2003 (DE) .................................. 103 16 583

(51) Int. Cl.
*G01N 33/543* (2006.01)
*G01N 33/574* (2006.01)
*G01N 33/68* (2006.01)
*G01N 33/74* (2006.01)

(52) U.S. Cl.
CPC ..... *G01N 33/54306* (2013.01); *G01N 33/574* (2013.01); *G01N 33/6893* (2013.01); *G01N 33/74* (2013.01); *G01N 2800/26* (2013.01)

(58) Field of Classification Search
None
See application file for complete search history.

(56) References Cited

U.S. PATENT DOCUMENTS

| 4,988,675 | A  | * | 1/1991  | Froesch ............... A61K 38/30 514/4.8 |
| 5,702,910 | A  | * | 12/1997 | Numata et al. ............. 435/7.94 |
| 5,786,163 | A  | * | 7/1998  | Hall ............................. 435/7.92 |
| 6,020,212 | A  |   | 2/2000  | Mathis |
| 6,440,421 | B1 | * | 8/2002  | Cornish ............... C07K 14/575 424/185.1 |
| 6,756,483 | B1 |   | 6/2004  | Bergmann et al. |
| 6,849,714 | B1 | * | 2/2005  | Bridon et al. ................ 530/335 |
| 6,887,470 | B1 | * | 5/2005  | Bridon et al. ............. 424/133.1 |
| 7,300,664 | B1 | * | 11/2007 | Jossifoff ............... A61K 9/0007 424/434 |
| 7,915,002 | B2 | * | 3/2011  | Bergmann .................... 435/7.1 |
| 8,507,210 | B2 | * | 8/2013  | Bergmann et al. ........... 435/7.1 |
| 9,012,151 | B2 | * | 4/2015  | Ng .................... G01N 33/6893 424/139.1 |
| 9,116,153 | B2 | * | 8/2015  | Struck ..................... C07K 7/16 |
| 2002/0098195 | A1 | * | 7/2002  | Goeke .................. A61K 38/26 424/184.1 |
| 2002/0197596 | A1 | * | 12/2002 | Cooper ............. G01N 33/6893 435/4 |
| 2003/0109420 | A1 | * | 6/2003  | Valkirs et al. .................... 514/2 |
| 2003/0138377 | A1 | * | 7/2003  | Leyland-Jones ....... B82Y 30/00 424/9.2 |
| 2007/0082363 | A1 | * | 4/2007  | Bougueleret et al. ......... 435/7.1 |

FOREIGN PATENT DOCUMENTS

| EP | 0 622 458 A2 | 11/1994 |
| EP | 0 656 121 BI | 3/1998 |
| JP | H07-196693 | 8/1995 |
| JP | H11-508357 | 7/1999 |
| JP | 2002-527753 | 8/2002 |
| WO | WO 00/22439 | 4/2000 |
| WO | WO/00/69900 | 11/2000 |
| WO | WO 2002/08723 A2 | 1/2002 |

OTHER PUBLICATIONS

Harlow, E. and Lane, D., Antibodies: A Laboratory Manual (1988) Cold Spring Harbor Laboratory Press, Cold Spring Harbor, NY, pp. 53, 60-61, 72-76, and 578-579.*
Hrubec et al. "Plasma Versus Serum: Specific Differences in Biochemical Analyte Values" Journal of Avian Medicine and Surgery 16(2):101-105, 2002.*
Mathis et al. "Probing Molecular Interactions with Homogeneous Techniques Based on Rare Earth Cryptates and Fluorescence Energy Transfer" Clin. Chem. 41/9, 1391-1397 (1995).*
Enomoto et al. ("High throughput screening for human interferon-gamma production inhibitor using homogenous time-resolved fluorescence" J Biomol Screen. Aug. 2000;5(4):263-8).*
Kuby et al. Immunology, W.H. Freeman and Company (1992), p. 125.*
Bost et al. Immunol. Invest. 1988; 17:577-586.*

(Continued)

*Primary Examiner* — Christine Foster
(74) *Attorney, Agent, or Firm* — Millen White Zelano and Branigan, PC; John Sopp; Csaba Henter

(57) ABSTRACT

Method for the determination of adrenomedullin immunoreactivity in biological fluids for diagnostic purposes, in particular in sepsis, cardiac and cancer diagnosis, in which the midregional partial peptide (mid-proAM; SEQ ID NO:3) of proadrenomedullin, which comprises the amino acids (45-92) of the complete preproadrenomedullin (pre-proAM; SEQ ID NO:1), is measured in particular by means of an immunoassay which operates with at least one labelled antibody which specifically recognizes a sequence of mid-proAM.

2 Claims, 2 Drawing Sheets

(56) References Cited

OTHER PUBLICATIONS

Bendayan, M. J. Histochem. Cytochem. 1995; 43:881-886.*
Wolfe, S.L., Molecular and Cellular Biology, 1993, pp. 790-793.*
The Academic Press Dictionary of Science and Technology, definition for the term "polyclonal"; Oxford: Elsevier Science & Technology (1996); retrieved Oct. 22, 2008, from http://www.credoreference.com/entry/3144515/.*
Janeway et al. Immunobiology: the Immune System in Health and Disease (1999), Elsevier Science Ltd/Garland Publishing, New York, NY, Fourth Edition, pp. 34-35.*
Tikhonov et al. Neph. Dial. Transplant. 12(12):2557-61 (1997).*
Merck Manuals Online Medial Library, section index for "Heart and Blood Vessel Disorders"; Home Edition, retrieved from www.merck.com/mmhe on Mar. 29, 2008, 2 pages.*
Richards et al. "Plasma N-Terminal Pro-Brain Natriuretic Peptide and Adrenomedullin" Circulation 1998;97;1921-1929.*
Qi et al. "Effects of different peptide fragments derived from proadrenomedullin on gene expression of adrenomedullin gene" Peptides 23 (2002) 1141-1147.*
Kennedy et al. "Expression of the Rat Adrenomedullin Receptor or a Putative Human Adrenomedullin Receptor Does Not Correlate with Adrenomedullin Binding or Functional Response" Biochemical and Biophysical Research Communications 244, 832-837 (1998).*
Harlow, E. and Lane, D., Antibodies: A Laboratory Manual (1988) Cold Spring Harbor Laboratory Press, Cold Spring Harbor, NY, pp. 53, 60-61, 72-76, 555, 559, 561, and 578-579.*
Bollheimer et al. "Intracellular Depletion of Insulin by Oleate Is Due to an Inhibited Synthesis and Not to an Increased Secretion" Biochemical and Biophysical Research Communications 287, 397-401 (2001).*
Richards et al. "Plasma N-Terminal Pro-Brain Natriuretic Peptide and Adrenomedullin" Journal of the American College of Cardiology vol. 37, No. 7, 2001, pp. 1781-1787.*
Andreotti et al. "Immunoassay of Infectious Agents", Biotechniques. Oct. 2003;35(4):850-9.*
Diamandis et al. "Immunoassay", Academic Press, Jun. 21, 1996, ISBN: 0122147308, pp. 47-49.*
Ehlenz, K., et al., "High levels of circulating adrenomedullin in severe illness: Correlation with C-reactive protein and evidence against the adrenal medulla as site of origin", Exp Clin Endocrinol Diabetes, vol. 105, pp. 156-162 (1997).
Eto, T., "A review of the biological properties and clinical implications of adrenomedullin and proadrenomedullin N-terminal 20 peptide (PAMP), hypotensive and vasodilating peptides", Peptides, vol. 22, pp. 1693-1711 (2001).
Hinson, et al., "Adrenomedullin, a Multifunctional Regulatory Peptide", Endocrine Reviews, vol. 21(2), pp. 138-167 (2000).
Hirata, et al., "Increased Circulating Adrenomedullin, a Novel Vasodilatory Peptide, in Sepsis", Journal of Clinical Endocrinology and Metabolism, vol. 81(4), pp. 1449-1453 (1996).
Kitamura, K., et al., "The intermediate form of glycine-extended adrenomedullin is the major circulating molecular form in human plasma", Biochem. Biophys. Res. Commun., vol. 244(2), pp. 551-555 (1998). Abstract Only.
Kitamura, K., et al., "Adrenomedullin (11-26): a novel endogenous hypertensive peptide isolated from bovine adrenal medulla", Peptides, vol. 22, pp. 1713-1718, (2001).
Kohno, M., et al., "Plasma adrenomedullin concentrations in essential hypertension", Hypertension, vol. 27(1), pp. 102-107 (1996).
Kuwasako, K., et al., "Purification and characterization of PAMP-12 (PAMP-20) in porcine adrenal medulla as a major endogenous biologically active peptide", FEBS Lett, vol. 414(1), pp. 105-110 (1997). Abstract Only.
Kuwasako, K., et al., "Increased plasma proadrenomedullin N-terminal 20 peptide in patients with essential hypertension", Ann. Clin. Biochem., vol. 36 (Pt. 5), pp. 622-628 (1999). Abstract Only.
Lewis, L., et al., "Adrenomedullin (I-52) measured in human plasma by radioimmunoassay: plasma concentration, adsorption, and storage", Clinical Chemistry, vol. 44(3), pp. 571-577 (1998).
Pio, R., et al., "Complement Factor H is a Serum-binding Protein for Adrenomedulli, and the Resulting Complex Modulates the Bioactivities of Both Partners", The Journal of Biological Chemistry, vol. 276(15), pp. 12292-12300 (2001).
Editorial, Takahashi, K., "Adrenomedullin: from a pheochromocytoma to the eyes", Peptides, vol. 22, p. 1691 (2001).
Tomoda, Y., et al., "Regulation of adrenomedullin secretion from cultured cells", Peptides, vol. 22, pp. 1783-1794 (2001).
Tsuruda, T., et al., "Secretion of proadrenomedullin N-terminal 20 peptide from cultured neonatal rat cardiac cells", Life Sci., vol. 69(2), pp. 239-245 (2001). Abstract Only.
Wang, P., "Andrenomedullin and cardiovascular responses in sepsis", Peptides, vol. 22, pp. 1835-1840 (2001).
Washimine, H., et al., "Plasma concentration of human adrenomedullin in patients on hemodialysis", Clin. Nephrol., vol. 44(6), pp. 389-393 (1995). Abstract Only.
Kitamura, K., et al., "Adrenomedullin: A Novel Hypotensive Peptide Isolated From Human Pheochromocytoma", Biochemical and Biophysical Research Communications, vol. 192 (2), pp. 553-560 (1993).
Kitamura, K., et al., "Cloning and Characterization of cDNA Encoding a Precursor for Human Adrenomedullin", Biochemical and Biophysical Research Communications, vol. 194 (2), pp. 720-725 (1993).
Meisner, M., "Procalcitonin", Georg Thieme Verlag, ISBN 3-13-105473-5, p. 22 (2000).
Ueda, Shiro, et al., Increased Plasma Levels of Adrenomedullin in Patients with Systemic Inflammatory Response Syndrome, Am. J. Respir. Care Med., vol. 160, pp. 132-136, 1999.
Struck, Joachim, et el., Identification of an Adrenomedullin precursor fragment in plasma of sepsis patients, Peptides, 25, pp. 1369-1372, 2004.
"Adrenomedullin (AM(ADM) (45-92), Pro(Human) Product Spec Sheet; Phoenix Pharmaceuticals; Jan. 2010".
Office Action issued for Japanese Patent Application No. 2006-504400—dated Jun. 17, 2009, with translation, 8 pages.
Kitamura, K., et al., "Adrenomedullin and PAMP: Discovery, Structures, and Cardiovascular Functions," Microscopy Research and Technique 57:3-13 (2002).
Ehlenz, K., et al., "High Levels of Circulating Adrenomedullin in Severe Illness: Correlation with C-Reactive Protein and Evidence Against the Adrenal Medulla as Site of Origin," Endocrinoligy & Diabetes, 1997.
Morgenthaler, N.G., et al., "Measurement of Midregional Proadrenomedullin in Plasma with an Immunoluminometric Assay," Clin. Chem., 51:10, 1823-1829 (2005).
Cyr, Melanie, et al., "Bradykinin and des-$Arg^9$-bradykinin metabolic pathways and kinetics of activation of human plasma," Am J Physiol Heart Circ Physiol 281 :H275-H283, 2001.
Domschke, S., et al., "Vasoactive intestinal peptide in man: pharmacokinetics, metabolic and circulatory effects[1]," Gut, 1978, 19, 1049-1053.
Hunt, P.J., et al., Bioactivity and Metabolism of C-Type Natriuretic Peptide in Normal Man*, J of Clin Endocr and Metab, vol. 78, No. 6, 1428-1435.
Japp, A.G., et al., "Vascular Effects of Apelin in Vivo in Man," Journal of the American College of Cardiology (JACC), downloaded from content.onlinejacc.org on Apr. 5, 2011, JACC, vol. 52, No. 11, 2008, Sep. 9, 2008, 908-913.
Kimura, K., et al., "ANP is cleared much faster than BNP in patients with congestive heart failure," Eur J Clin Pharmacol (2007) 63:699-702.
Kitamura, K., et al., "Identification and hypotensive activity of proadrenomedullin N-terminal 20 peptide (PAMP)," FEBS Letters 351 (1994) 35-37.
Kraenzlin, M.E., et al., "Infusion of a novel peptide, calcitonin gene-related peptide (CGRP) in man. Pharmacokinetics and effects on gastric acid secretion and on gastrointestinal hormones," Regulatory Peptides, 10 (1985) 189-197.
Lundberg, J.M., et al., "Evidence for Release of Endothelin-1 in Pigs and Humans," Journal of Cardiovascular Pharmacology, 17 (Suppl. 7):S350-S353.

(56) References Cited

OTHER PUBLICATIONS

Magness, R.R., Ph.D., et al., "Angiotensin II metabolic clearance rate and pressor responses in nonpregnant and pregnant women," Am J Obstet Gynecol, vol. 171, No. 3, 668-679.

Meeran, K., et al., "Circulating adrenomedullin does not regulate systemic blood pressure but increases plasma prolactin after intravenous infusion in humans: a pharmacokinetic study," J Clin Endocrinol Metab, 1997; 82:95-100.

Webster's New World Dictionary (of the American Language), Second College Edition, 1982, p. 1568.

Beltowski, J., et al., "Adrenomedullin—What do we know 10 years since its discovery?" Polish Journal of Pharmacology, 2004, 56, 5-27.

Etoh, T., et al., "Differential Hormonal Profiles of Adrenomedullin and Proadrenomedullin N-terminal 20 Peptide in Patients with Heart Failure and Effect of Treatment on Their Plasma Levels," Clin. Cardiol. 22, 113-117 (1999).

Hamada, H., et al., "Plasma adrenomedullin and proadrenomedullin N-terminal 20 peptide in patients diagnosed as having early rheumatoid arthritis," Mod Rheumatol (2010) 20: 389-395.

Nagatomo, Y., et al., "Proadrenomedullin N-Terminal 20 Peptide is Rapidly Cleaved by Neutral Endopeptidase," Biochemical and Biophysical Research Communications, 223, 539-543 (1996).

Uemura, T., et al., "Aldosterone augments adrenomedullin production without stimulating pro-adrenomedullin N-terminal 20 peptide secretion in vascular smooth muscle cells," Journal of Hypertension, vol. 20, No. 6, 1209-1214, (2002).

Harlow and Lane (Antibodies: A Laboratory Manual (1988) Cold Spring Harbor Laboratory Press, Cold Spring Harbor, NY, pp. 23-24 and 76).

Geysen ("Cognitive Features of Continuous Antigenic Determinants", J Mol Recognit. Feb. 1988;1(1):32-41.

NCBI, "Adrenomedullin Precursor", UnkProtKB/Swiss-Prot: P35318 (Nov. 1, 1997), retrieved from http://www.ncbi.nlm.nih.gov/protein/461474?sat=8&satkey=1020578 on Feb. 25, 2016, two pages.

* cited by examiner

DETERMINATION OF A MIDREGIONAL PROADRENOMEDULLIN PARTIAL PEPTIDE IN BIOLOGICAL FLUIDS FOR DIAGNOSTIC PURPOSES, AND IMMUNOASSAYS FOR CARRYING OUT SUCH A DETERMINATION

CROSS REFERENCE TO RELATED APPLICATIONS

This application is a 371 filing of PCT International application no. PCT/EP2004/000806 filed Jan. 29, 2004 and published in German as WO 2004/090546 on Oct. 21, 2004 which claims the priority of German application no. 103 16 583.5 filed Apr. 10, 2003, the disclosures of which are hereby incorporated by reference in their entirety.

The invention relates to methods for determining a midregional partial peptide of proadrenomedullin (mid-proAM), in particular the determination of the proAM (45-92) partial peptide in biological fluids for purposes of medical diagnosis, and in particular in the diagnosis of sepsis, but also, for example, in cancer diagnosis and cardiac diagnosis or generally in the diagnosis of those pathological states in which a determination of the peptide adrenomedullin (AM) gives diagnostically relevant results. The determinations according to the invention are carried out in particular by means of immunoassays of a type in which a labelled antibody is employed (sandwich assay; competitive assay according to the SPALT or SPART principle).

In this description, the term "diagnosis" is used in principle as a simplifying general term which is also intended to include prognosis/early prognosis and therapy-accompanying monitoring.

The peptide adrenomedullin (AM) was described for the first time in 1993 by Kitamura et al. (cf. 18; numerical data are based on the attached list of references) as a novel hypotensive peptide comprising 52 amino acids, which had been isolated from a human phenochromocytome. In the same year, cDNA coding for a precursor peptide comprising 185 amino acids and the complete amino acid sequence of this precursor peptide were also described (19; SEQ ID NO:1). The precursor peptide, which comprises, inter alia, a signal sequence of 21 amino acids at the N-terminus, is referred to as "preproadrenomedullin" (pre-proAM). In the present description, all amino acid positions specified usually relate to the pre-proAM which comprises the 185 amino acids and has the sequence according to SEQ ID NO:1, unless something different is evident from the specific context of the text.

The peptide adrenomedullin (AM) is a peptide which comprises 52 amino acids (SEQ ID NO:2) and which comprises the amino acids 95 to 146 of pre-proAM, from which it is formed by proteolytic cleavage. To date, substantially only a few fragments of the peptide fragments formed in the cleavage of the pre-proAM have been more exactly characterized, in particular the physiologically active peptides adrenomedullin (AM) and "PAMP", a peptide comprising 20 amino acids (22-41) which follows the 21 amino acids of the signal peptide in pre-proAM. For both AM and PAMP, physiologically active sub-fragments have furthermore been discovered and investigated in more detail.

The discovery and characterization of AM in 1993 triggered intensive research activity and a flood of publications, the results of which have recently been summarized in various review articles, in the context of the present description, reference being made in particular to the articles to be found in an issue of "Peptides" devoted to AM (Peptides 22 (2001)), in particular (12) and (2). A further review is (3). In the scientific investigations to date, it has been found, inter alia, that AM may be regarded as a polyfunctional regulatory peptide. It is released into the circulation in an inactive form extended by glycine (5). There is also a binding protein (11) which is specific for AM and probably likewise modulates the effect of AM.

Those physiological effects of AM as well as of PAMP which are of primary importance in the investigations to date were the effects influencing blood pressure. Thus, AM is an effective vasodilator, it being possible to associate the hypotensive effect with in particular peptide segments in the C-terminal part of AM. Peptide sequences of the N-terminus of AM on the other hand exhibit hypertensive effects (cf. for example (6)).

It has furthermore been found that the above-mentioned further physiologically active peptide PAMP formed from pre-proAM likewise exhibits a hypotensive effect, even if it appears to have an action mechanism differing from that of AM (cf. in addition to the above-mentioned review articles (2) and (3) also (8), (9) or (14) and EP 0 622 458 A2).

It has furthermore been found that the concentrations of AM which can be measured in the circulation and other biological fluids are, in a number of pathological states, significantly above the concentrations to be found in healthy control persons. Thus, the AM level in patients with congestive heart failure, myocardial infarction, kidney diseases, hypertensive disorders, Diabetes mellitus, in the acute phase of shock and in sepsis and septic shock are significantly increased, although to different extents (cf. for example (2), Section 7, and the literature cited in this context). The PAMP concentrations are also increased in some of said pathological states, but the plasma levels are reduced relative to AM ((2); page 1702).

It is furthermore known that unusually high concentrations of AM are to be observed in sepsis or in septic shock (cf. (2) and (4), (1), (13), (15) and (16)). The findings are related to the typical haemodynamic changes which are known as typical phenomena of the course of a disease in patients with sepsis and other severe syndromes, such as, for example, SIRS.

Although it is assumed that AM and PAMP are formed from the same precursor peptide, pre-proAM (SEQ ID NO:1), in which the amino acid sequences corresponding to these peptides are present as partial peptides in equimolar amounts, the concentrations of AM or PAMP measurable in biological fluids apparently differ. This is nothing unusual. Thus, the measurable concentrations of different degradation products of one and the same precursor peptide may be different, for example, because they are the result of different competing degradation pathways which, for example in the case of different pathological states, lead to different fragmentation of a precursor peptide and hence to different degradation products. Certain partial peptides contained in the precursor peptide may be formed as free peptides or may not be formed, and/or different peptides are formed in different ways and in different amounts. Even if only a single degradation pathway is taken for processing a precursor peptide, and hence all degradation products originate from one and the same precursor peptide and must have been formed per se primarily in equimolar amounts, the steady-state concentrations of different partial peptides and fragments measurable in biological fluids may be very different, namely, for example, when individual ones thereof are formed at a different rate and/or have different individual stabilities (lifetimes) in the respective biological fluid, or if they are removed from circulation on the basis of different clearance mechanisms and/or at different clearance rates.

Thus, it is true that, in connection with the formation of AM, it may be assumed that, in addition to AM and PAMP, other peptide fragments must also be formed in the proteolytic processing of pre-proAM. However, the scientific literature contains no data at all on the occurrence and on the stability of such possible further fragments, even though peptides corresponding to such pre-proAM peptide fragments and also radioimmunoassays (RIA) for their determination are commercially available for research purposes, for example from Phoenix Pharmaceuticals, Inc.

On the basis of knowledge which had been gained with the occurrence of the prohormone procalcitonin in sepsis (cf. for example EP 0 656 121 B1), and starting from the hypothesis that other prohormones usually not observable might possibly also be detectable in the case of sepsis in the circulation of sepsis patients, the Applicant carried out an exploratory experiment on the detection of proadrenomedullin in sera of sepsis patients using a commercially available RIA with an antibody which binds to the amino acids 45-92 of pre-proAM but not to sequences of mature AM. The results, which are described in the publication WO 00/22439, show a concentration of an analyte provisionally designated as proadrenomedullin which is increased compared with healthy control persons. However, the measured increase was only of the order of magnitude of about twice the normal value, i.e. was relatively small. In view of literature data which report increased AM values of the order of magnitude of 12 times the normal value in the case of sepsis, the observed increase to about twice the normal value for the proAM immunoreactivity measured with the assay used did not appear very attractive for determining this "proAM immunoreactivity" instead of AM in sepsis diagnosis. Whether proadrenomedullin (22-185 or 22-146) was actually measured in the experiment described or whether the proadrenomedullin immunoreactivity measured in the manner described was attributable to one species or to a plurality of different species occurring in the patient samples could not be decided on the basis of the measured findings.

In the course of its comprehensive research and development work on biomarkers which may be of clinical use for sepsis diagnosis, and in particular in view of the aim of being able to improve fine sepsis diagnosis by the method of multiparameter determination (simultaneous determination of a plurality of biomarkers), the Applicant also considered the determination or additional determination of the AM which is increased in sepsis. However, as was found, a reliable determination of AM with the acquisition of results which would permit a simple comparison of measured results beyond the limits of the respective individual research work was not directly possible. The data for most research work were obtained using RIAs which were based on competition of AM with a labelled marker peptide for a common AM binding site of an antibody. The respective RIAs were often individual developments, and various antibodies and peptides were employed, making a quantitative interassay comparison of the measured results obtained more difficult (cf. for example 10). Moreover, recent research results had shown that there are various forms of AM (with or without C-terminal glycine residue), to which different activities could be assigned (cf. (2) and, for example, (5)). The discovery of a binding protein (cf. 11) for AM led to a further complication of the situation—both the present or absent glycine residue and the absent or present complexing of AM by its binding protein can influence the determination of AM as a function of the respective assay in an unpredictable manner. These circumstances set high requirements with regard to a valid immunoassay for AM which is suitable for routine investigations: for such an assay, it is necessary to find suitable antibodies which bind to those AM regions which are not occupied by the binding protein, if there are such regions at all. Alternatively, it is necessary to carry out a preceding step for the liberation and separation of the binding protein from AM, the influence of such a step on the stability of the AM and/or the measured values obtained being difficult to estimate. The fact that, in addition to the complete AM, different AM partial peptides are also found physiologically and appear to play a role in the overall physiological process further complicates the provision of a valid immunoassay and the comparability of the measured values appearing in the literature.

It is therefore the Applicant's object to provide a valid method which is suitable for routine procedures, is substantially insensitive to the above-mentioned interfering influences of a direct measurement of AM and is capable of giving reliable values for the physiological production of AM and/or its precursor in various pathological states, in particular sepsis or other pathological states, in which increased values are found for AM.

This object is achieved, according to the invention, if, instead of AM or another of the pre-proAM partial peptides investigated to date, a midregional partial peptide which contains the amino acids 45-92 of pre-proAM (SEQ ID NO:3) is determined for diagnostic purposes, the determination being particularly preferably effected using an immunoassay in which a labeled antibody is employed.

Claim 1 represents the core of the present invention.

Advantageous and currently preferred embodiments of the invention are described in the subclaims.

To achieve the object of providing an assay method which reliably measures the formation of AM or of its precursor products or byproducts in various pathological states, in particular sepsis, but also, for example, cardiac diseases, hypertensive disorders or cancers or other diseases, in which increased AM levels may be observed, on the one hand the result of a "proadrenomedullin immunoreactivity" increased during sepsis, which is described in WO 00/22439, was employed as a basis in spite of the not very promising results. On the other hand, supplementary comprehensive clinical studies with measurement of sera of sepsis, cancer and cardiac patients was carried out using various novel assays, which surprisingly gave measured values having substantially improved validity.

The investigations carried out and the most significant results of these investigations are explained in more detail below, reference being made to figures.

FIG. 1 shows the results of the measurement of mid-proAM in sera of 109 healthy normal persons, compared with the results of the measurement of 110 sera of sepsis patients and of 20 sera of patients with polytrauma. All measurements were carried out by means of a SPALT assay, as described in more detail in the experimental section. It is remarkable that—in contrast to the case of procalcitonin and other inflammation markers—only the values for the sepsis patients (high concentrations of about 550 pmol/l and 550 fmol/l compared with values of 33 pmol/l for healthy persons) were increased but not the values for polytrauma patients.

FIG. 2 shows the results of the measurement of mid-proAM in sera of 274 healthy normal persons, of 267 sepsis patients, of 20 patients with cardiac diseases and 49 cancer patients using a sandwich assay as described in more detail in the experimental section.

In connection with the investigation which led to the present invention, the question as to the nature of the species measured in the various diseases or as to the choice of a particularly suitable species for AM/proAM measurements was of primary importance. Since RIAs are in principle not very suitable for delivering valuable knowledge on this question, and moreover, for various reasons, RIAs also do not appear very promising for the development aim of providing a valid assay for routine determinations, it was first necessary to develop novel assays, immunoassays of the type in which labelled antibodies could be employed being chosen.

In the investigation of the question as to whether the increased values for a proadrenomedullin immunoreactivity in sepsis, which are measured according to WO 00/22439, actually reflect increased proadrenomedullin concentrations in the samples investigated, a sandwich assay was first developed which, on the basis of the assay design, was substantially specific for proadrenomedullin (22-146 or 22-185) in that it could recognize neither AM nor pre-proAM partial peptides which contained no AM.

This sandwich assay employed two different antibodies which specifically recognized the amino acid sequence of the peptide (69-86: peptide range SPCD19; SEQ ID NO:4) or of a peptide (129-147; C-terminal AM peptide). The standard material used was the recombinant complete proadrenomedullin (22-185), which had been calibrated in a commercial competitive AM assay.

In the measurement of sera of healthy normal persons and of sepsis patients, no increased measured values above the detection limit of about 40 pg/ml were obtained using this sandwich assay (results not shown). From these findings, it was necessary to draw the conclusion that the increased proAM immunoreactivity found in the case of sepsis is not due to the presence of the proadrenomedullin peptide in the samples.

For further checking of the question as to whether the relatively slightly (about two-fold) increased "proAM immunoreactivity measured values" of the earlier measurements had been real or whether artifacts due to the commercial RIA used might have played a role in these measurements, a further assay based on the so-called SPALT principle was developed. In such an assay, a competition between a solid phase-bound (solid phase=SP) competitor for the analyte ("antigen"=A) and the analyte for common binding sites of a labelled antibody which is present in the reaction fluid is utilized. In the present case, the antibody was labelled with a luminescence tracer (LT) (cf. experimental section). The presence of the analyte or the occupancy of binding sites of the antibody by competing binding partners from the sample is evident as a reduction in the binding of the labelled antibody to the solid phase.

The solid phase-bound competitor used in the SPALT assay described was the solid phase-bound peptide (69-86: peptide range SPCD19; SEQ ID NO:4), and the antibody used was a labelled anti-SPCD19-sheep antibody formed against this peptide and recognizing this peptide (affinity-purified; cf. experimental section). The standard used comprised dilutions of the peptide SPCD19 in normal horse serum. The limit of detection was about 50 pmol/l. In the determinations, in each case 100 μl of sample (standard) and 100 μl of tracer were incubated overnight at 4° C. in Polysorb tubes coated with the SPCD19 peptide, after which washing was effected with 4×1 ml of standard wash solution from the Applicant's LUMItest® and then measurement was effected in a luminometer.

During a measurement of sepsis by means of this SPALT assay, a dramatic distinction between sepsis patients and healthy normal persons was found. At a limit of detection of about 1 ng/ml, sera of sepsis patients gave values which were on average about 19000 pg/ml. The substantial difference between sera of sepsis patients and healthy persons was very surprising in view of the fairly slight increase in the preliminary experiments using a commercial RIA (WO 00/22439).

The clinical measurements by means of said SPALT assay were extended. The results of the extended study are summarized graphically in FIG. 1, express reference being made to the above explanation of FIG. 1.

The above-mentioned positive results using SPALT assays showed that (i) the "proAM-immunoreactivity" measured in sepsis sera could not be attributed to the actual presence of proadrenomedullin, but (ii) a corresponding measurement of an analyte having an amino acid sequence from a middle segment of pre-proAM, more precisely the mid-proAM according to SEQ ID NO:3, was suitable for clearly distinguishing sepsis patients from normal persons.

On the basis of these results, the investigation was extended in two directions:
1. The pre-proAM species actually occurring in the circulation was to be identified and optionally investigated with regard to its suitability as a biomarker for routine measurements.
2. At the same time, the extent to which the measurement of these species gives diagnostically valuable measured results was to be further investigated.

The results are described in more detail below with reference to the experimental section. They can be summarized as follows:
1. A peptide which contains the amino acids 45-92 of pre-proAM or consists thereof (SEQ ID NO:3) and which is referred to in this Application as mid-proAM is present in significantly increased concentration, and well reproducible measurability, in the circulation (serum, plasma).
2. The measurement of sera of patients by means of an assay which specifically measures this mid-proAM gives measured results which not only permit a clear distinction between sepsis patients and normal persons but—in combination with clinical findings—also enable the detection of other diseases which are associated with increased formation of AM, in particular cardiac and cancer diseases.

The method therefore relates in particular to the determination of mid-proAM in the circulation of a patient, in particular using plasma samples.

Certain general aspects of preferred embodiments of the invention are also explained in more detail below, and further selected experimental results are explained in more detail.

For the practical implementation of the invention, an assay format is preferred in which labelled antibodies are employed, e.g. an assay which operates according to the competitive SPALT principle described above (but other labels, for example radioactive ones in the form of an SPART assay, can also be used).

However, noncompetitive sandwich assays, for example of the type as used for the further more extensive investigations and described in more detail below, are particularly preferred.

Compared with competitive immunoassays, noncompetitive sandwich immunoassays (two-sided immunoassays) have a number of advantages which include the fact that they can be better designed than solid phase assays (heterogeneous assays), can be more robust in terms of handling, can give measured results having a higher sensitivity and are also more suitable for automation and series measurement. Moreover, they can also give additional information compared with competitive immunoassays which operate with only one type of antibody, in that sandwich immunoassays recognize only those molecules or peptides in which both binding sites for the antibodies used for the sandwich formation are present on the same molecule.

The antibodies can in principle be any suitable monoclonal and/or polyclonal antibodies, but affinity-purified polyclonal antibodies are currently preferred.

Particularly preferably, one of the antibodies is obtained by immunizing an animal, in particular sheep, with an antigen which contains a synthetic peptide sequence which has the amino acids 69-86 of pre-proAM and an additional cysteine residue on the N-terminus (SEQ ID NO:4). The other antibody can accordingly be obtained, for example, with an antigen which contains a synthetic peptide sequence which has the amino acids 83-94 (peptide range PSR13; SEQ ID NO:5) of the pre-proAM with an additional cysteine residue at the N-terminus. The antibodies obtained using said synthetic peptides, which together cover a continuous midregional segment of the proAM sequence, recognize only binding sites in the region of the above-mentioned mid-proAM (amino acids 45-92), more precisely in the region of the amino acids 60-92 of pre-proAM.

In principle, all labeling techniques which are used in assays of the type described can be employed, which techniques include labeling with radioisotopes, enzymes, fluorescent, chemiluminescent or bioluminescent labels and directly optically detectable colour labels, such as, for example, gold atoms and dye particles, as used in particular for so-called point-of-care (POC) or quick tests. In the case of heterogeneous sandwich immunoassays, too, the two antibodies may have parts of a detection system of the type described below in connection with homogeneous assays.

In principle, all labelling techniques which are used in assays of the type described can be employed, which techniques include labelling with radioisotopes, enzymes, fluorescent, chemoluminescent or bioluminescent labels and directly optically detectable color labels, such as, for example, gold atoms and dye particles, as used in particular for so-called point-of-care (POC) or quick tests. In the case of heterogeneous sandwich immunoassays, too, the two antibodies may have parts of a detection system of the type described below in connection with homogeneous assays.

The present invention therefore also relates to the design of the method according to the invention as a quick test.

The method according to the invention can furthermore be designed as a homogeneous method in which the sandwich complexes formed from the two antibodies and the mid-proAM to be detected remain suspended in the liquid phase. In such a case, it is preferable to label both antibodies with parts of a detection system which, when both antibodies are integrated in a single sandwich, permit signal generation or signal triggering. Such techniques can be designed in particular as fluorescence amplification or fluorescence extinction detection methods. A particularly preferred method of this type relates to the use of detection reagents to be used in pairs, as described, for example, in U.S. Pat. No. 4,822,733, EP-B1-180 492 or EP-B1-539 477 and the prior art cited therein. They permit a measurement which selectively detects only reaction products which contain both labelling components in a single immune complex, directly in the reaction mixture. As an example, reference is made to the technology offered under the brands TRACE® (Time Resolved Amplified Cryptate Emission) and KRYPTOR®, which implement the teachings of the above-mentioned Applications.

It has surprisingly been found that the determination, according to the invention, of mid-proAM (SEQ ID NO:3) gives highly significant measured results. As will be shown below, this statement applies not only to the diagnosis of sepsis but also to cardiac diagnosis and cancer diagnosis.

It is assumed that the determination method according to the invention can be particularly advantageously carried out also in the course of a so-called multiparameter diagnosis, in particular both in the area of cardiac diagnosis and in the area of sepsis and cancer diagnosis. Further parameters determined thereby are, for example, the cardiac parameters ANP, BNP, proANP or proBNP or sepsis parameters which are selected, for example, from the group consisting of anti-ganglioside antibodies, the proteins procalcitonin, CA 125, CA 19-9, S100B, S100A proteins, LASP-1, soluble cytokeratin fragments, in particular CYFRA 21, TPS and/or soluble cytokeratin-1 fragments (sCY1F), the peptides inflammin and CHP, other peptide prohormones, glycine-N-acyltransferase (GNAT), the carbamoyl phosphate synthetase 1 (CPS 1) and the C-reactive protein (CRP) or fragments thereof. In the case of said multiparameter determinations, it is intended to determine the measured results for a plurality of parameters simultaneously or in parallel and to evaluate them, for example, with the aid of a computer program which also utilizes diagnostically significant parameter correlations.

Figure 1:
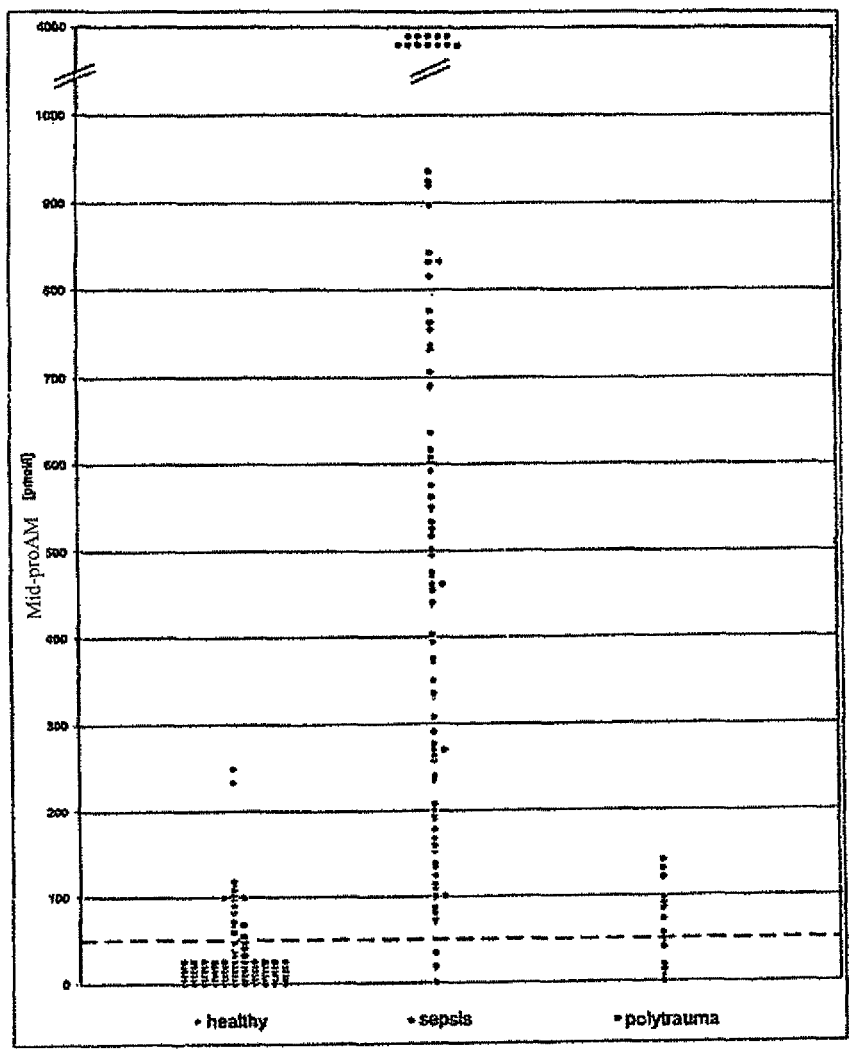
FIG. 1 shows measured amounts of mid-proAM in various classes of subjects.

The invention is explained in more detail below by a description of the preparation of the preferred assay components, the procedure for a preferred embodiment of an assay of the sandwich type and the results of mid-proAM determinations in EDTA plasmas of control persons and of sepsis, cardiac and cancer patients, which results are obtained using such an assay.

Furthermore, the identification of the proAM partial peptide actually determined and occurring in the circulation is described.

Experimental Section

Material and Methods

1. Peptide Syntheses

Derived from the known amino acid sequence of human preproadrenomedullin (SEQ ID NO:1), a first range (Pos. 69-86: peptide range SPCD19; SEQ ID NO:4) and a second range (Pos. 83-94: peptide range PSR13; SEQ ID NO:5) was selected. Supplemented in each case by a N-terminal cysteine residue, both ranges were chemically synthesized by standard methods as soluble peptides, purified, subjected to quality control by means of mass spectrometry and reversed phase HPLC, and lyophilized in aliquots (JERINI AG, Berlin, Germany). The amino acid sequences of the peptides are:

```
Peptide SPCD19:   CRPQDMKGASRSPEDSSPD  (SEQ ID NO: 4)

Peptide PSR13:    CSSPDAARI RVKR       (SEQ ID NO: 5)
```

In addition, the entire mid-proAM (corresponding to Pos. 45-92; SEQ ID NO:3) were synthesized as standard:

(SEQ ID NO: 3)
ELRMSSSYPTGLADVKAGPAQTLIRPQDMKGASRSPEDSSPDAARIRV

2. Conjugation and Immunization

The above peptides SPCD19 and PSR13 were conjugated to the carrier protein KLH (Keyhole limpet hemocyanin) by means of MBS (m-maleimidobenzoyl-N-hydroxysuccinimide ester) (cf. working instructions "NHS ester maleimide crosslinkers" from PIERCE, Rockford, Ill., USA). Sheep were immunized with these conjugates according to the following scheme: each sheep initially received 100 µg of conjugate (mass data based on the peptide fraction of the conjugate) and then 50 µg of conjugate at 4 week intervals (mass data based on the peptide fraction of the conjugate). Beginning with the fourth month after the beginning of the immunization, 700 ml of blood were taken per sheep at 4 week intervals and antiserum was obtained therefrom by centrifuging. Conjugations, immunizations and obtaining of antisera were carried out by Micropharm, Carmarthenshire, UK.

3. Purification of the Antibodies

In a 1-step method, the peptide-specific antibodies were prepared as follows from the antisera which had been obtained beginning with the fourth month after the immunization.

For this purpose, the above-mentioned peptides SPCD19 and PSR13 were first coupled to SulfoLink Gel (cf. working instructions "SulfoLink Kit" from PIERCE, Rockford, Ill., USA). In each case 5 mg of peptide per 5 ml of gel were offered for coupling.

The affinity purification of peptide-specific antibodies from sheep antisera against both peptides was carried out as follows:

The peptide columns were first washed three times alternately with 10 ml each of elution buffer (50 mM citric acid, pH 2.2) and binding buffer (100 mM sodium phosphate, 0.1% Tween, pH 6.8). 100 ml of the sheep antisera were filtered over 0.2 µm and mixed with the column material present. For this purpose, the gel was washed quantitatively with 10 ml of binding buffer out of the column. The incubation was effected overnight at room temperature with swirling. The batches were transferred quantitatively to empty columns (NAP 25, Pharmacia, emptied). The run-throughs were discarded. This was followed by washing protein-free with 250 ml of binding buffer (protein content of the wash eluate <0.02 A280 nm). Elution buffer was added to the washed columns, and 1 ml fractions were collected. The protein content of each fraction was determined by means of the BCA method (cf. working instructions from PIERCE, Rockford, Ill., USA). Fractions having protein concentrations >0.8 mg/ml were pooled. After a protein determination of the pools by means of the BCA method, yields of 49 mg for the anti-SPCD19 antibody (affinity-purified; polyclonal) and 60 mg for the anti-PSR13 antibody (affinity-purified; polyclonal) were obtained.

4. Labelling

Over an NAP-5 gel filtration column (Pharmacia), 500 µl of the purified anti-SPCD19 antibody (see above) were rebuffered in 1 ml of 100 mM potassium phosphate buffer (pH 8.0) according to the working instructions). The protein concentration determination of the antibody solution gave a value of 1.5 mg/ml.

For chemiluminescent labelling of the antibody, 10 µl of MA70 acridinium NHS ester (1 mg/ml; from HOECHST Behring) were added to 67 µl of the antibody solution and incubation was effected for 15 minutes at room temperature. Thereafter, 423 µl of 1 M glycine were added and incubation was effected for a further 10 minutes. Thereafter, the labelling batch was rebuffered over an NAP-5 gel filtration column (Pharmacia) in 1 ml of mobile phase A (50 mM potassium phosphate, 100 mM NaCl, pH 7.4) according to the working instructions and freed from low molecular weight components. For separating off final residues of labels not bound to antibodies, a gel filtration HPLC was carried out (column: Waters Protein Pak SW300). The sample was applied and was chromatographed at a flow rate of 1 ml/min using mobile phase A. The wavelengths 280 nm and 368 nm were measured with a flow photometer. The absorption ratio 368 nm/280 nm as a measure of the degree of labelling of the antibody was 0.10 at the peak. The monomeric fractions containing antibodies (retention time 8-10 min) were collected and were taken up in 3 ml of 100 mM sodium phosphate, 150 mM NaCl, 5% bovine serum albumin, 0.1% sodium azide, pH 7.4.

The labelled antibody was used on the one hand, as described in more detail below, in a sandwich immunoassay but, on the other hand, also in the SPALT assay already described.

5. Coupling

In order to provide the solid phase of a sandwich immunoassay, irradiated 5 ml polystyrene tubes (from Greiner) were coated with purified anti-PSR13 antibody as follows: the antibody was diluted to a concentration of 6.6 µg/ml in 50 mM Tris, 100 mM NaCl, pH 7.8. 300 µl of this solution were pipetted into each tube. The tubes were incubated for 20 hours at 22° C. The solution was filtered with suction. Each tube was then filled with 4.2 ml of 10 mM sodium phosphate, 2% Karion FP, 0.3% bovine serum albumin, pH 6.5. After 20 hours, the solution was filtered with suction. Finally, the tubes were dried in a vacuum dryer.

The labelling and immobilization procedures described were also carried out in substantially the same manner with the respective other antibody, an "inverse" sandwich assay being obtained. Determinations which were carried out analogously to the determinations described below using such an "inverse" labelled/immobilized immunoassay gave substantially identical results and are therefore not additionally described.

6. Carrying Out the Sandwich Immunoassay and Evaluation Thereof

An assay buffer having the following composition was prepared:

100 mM sodium phosphate, 150 mM NaCl, 5% bovine serum albumin, 0.1% unspecific sheep IgG, 0.1% sodium azide, pH 7.4

The standard material used was a chemically synthesized mid-proAM (SEQ ID NO:3). This peptide was diluted serially in normal horse serum (from SIGMA). The standards thus prepared were assigned concentrations according to the sample weight of peptide.

Measured samples were EDTA plasmas of apparently healthy persons, of patients with sepsis and of patients with cardiac and with cancer diseases.

10 µl of standards or samples and 200 µl of assay buffer, containing 1 million RLU (relative light units) of the MA70-labelled anti-SPCD19 antibody, were pipetted into the test tubes. Incubation was effected for two hours at 22° C. with shaking. Washing was then effected 4 times with 1 ml of wash solution each time (0.1% Tween 20) per tube, the latter were allowed to drip off and the chemiluminescence bound to the tube was measured in a luminometer (from BERTHOLD, LB952T; base reagents from BRAHMS AG).

Figure 2:
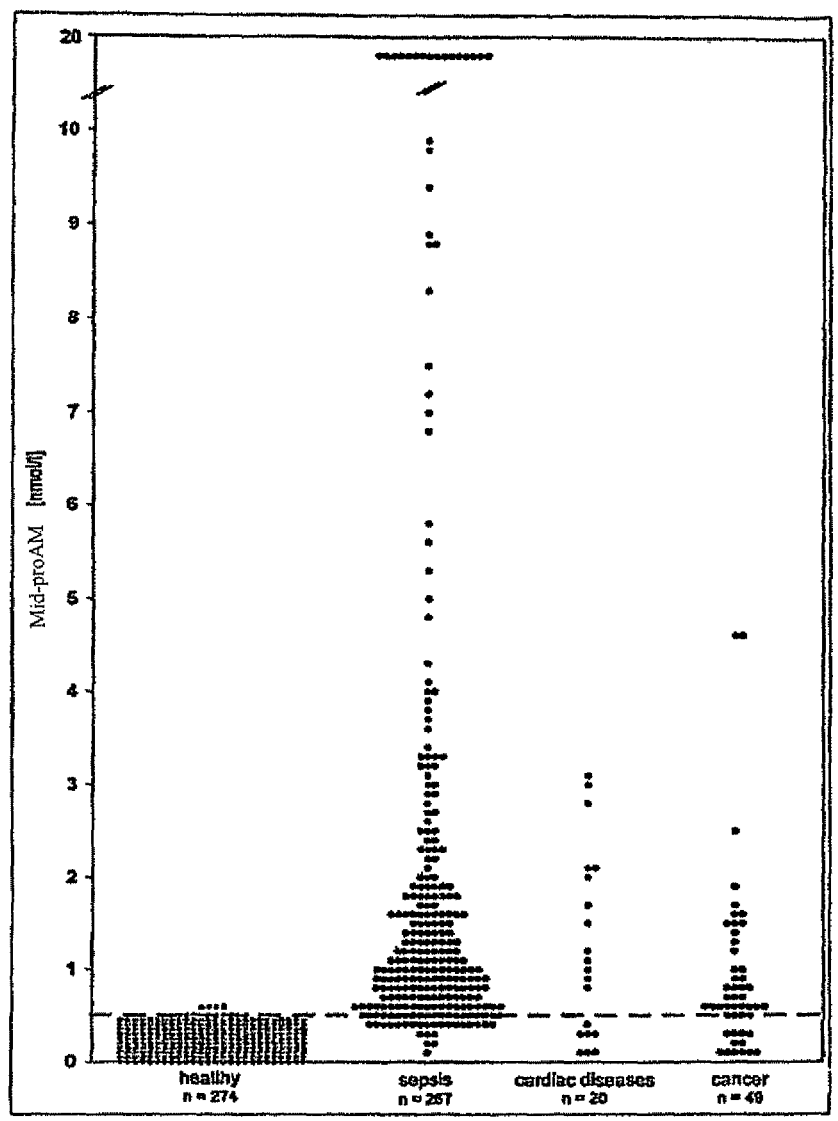
FIG. 2 shows measured amounts of mid-proAM in various classes of subjects.

Using the software MultiCalc (Spline Fit), the midregional proadrenomedullin concentrations of the samples were read from the standard curve. The results are summarized graphically in FIG. 2.

7. Carrying Out the SPALT Immunoassay and Evaluation Thereof

The solid phase-bound competitor used in the SPALT assay described was the solid phase-bound peptide SPCD19 (peptide range 69-86; SEQ ID NO:4), which had been bound to the walls of Polysorb tubes. The antibody used was the labelled anti-SPCD19-sheep antibody (affinity-purified) obtained as described above under 1. to 4. Dilutions of the peptide SPCD19 in normal horse serum were used as a standard.

In the determinations, in each case 100 µl of sample (or standard) and 100 µl of tracer were incubated overnight at 4° C. in the Polysorb tubes coated with the SPCD19 peptide, after which washing was effected with 4×1 ml of standard wash solution from the Applicant's LUMItest®, followed by measurement in the luminometer.

The results of a measurement series obtained using this assay are shown in FIG. 1.

8. Identification of the Analyte Measured in the Assays Described

For concentration of the analyte which is recognized by the antibody used in the above-mentioned assays, three individual sepsis plasmas were directly fractionated analytically via a C18 reverse phase HPLC, elution being effected by means of a linear acetonitrile gradient. 1 ml fractions were collected and dried. The fractions were taken up in assay buffer, and the SPCD19 immunoreactivity of the individual fractions was determined. For this purpose, an anti-SPCD19 antibody (cf. above under 3.) was immobilized on the walls of a Polysorb tube, and the competition of sample (fraction) and luminescence-labelled SPCD19 for this antibody was determined.

In such an analysis, it was found that, for all sepsis plasmas, the greatest immunoreactivity was to be found in the same fraction (fraction 22).

For further identification of the measured analyte, 7 sepsis sera of about 3 ml each were pooled (final volume 22 ml). Using a Carbolink column with an anti-SPCD19 antibody, the pooled sera were subjected to an affinity purification, and the acidic eluate was fractionated as above via a C18 reversed phase HPLC. Fraction 22 was dried and was investigated by mass spectrometry.

In a direct mass spectrometric analysis, a value of about 5146 Dalton was determined as the molar mass of the analyte isolated. This value corresponds to the molar mass of a proAM fragment which contains the amino acids of positions 45-92, i.e. of the mid-proAM (the theoretical value is 5146.72 Dalton, assuming that the two methionine residues present are oxidized).

In a MALDI-TOF analysis of the tryptic digestion of the isolated fraction 22, inter alia peptide fragments which correspond to the amino acids of positions 79-89, 75-89, 61-74 and 61-78 of pre-proAM were identified as monoisotopic masses (M+H$^+$). The molar mass data and the mass spectrometric analysis of the tryptic degradation together prove that the peptide contained in the isolated fraction is the peptide designated as mid-proAM (45-92) (SEQ ID NO:3). Its formation can be explained by proteolytic processing of the original pre-proAM translation product by signal peptidase, prohormone convertase (cleavage between basic amino acids) and amino- and carboxy-peptidase (elimination of the basic amino acids) (cf. the analogous scheme for the procalcitonin degradation in (20)).

9. Stability Investigation

For examining the question as to whether problems are likely in a measurement of mid-proAM because of insufficient stability of the mid-proAM in a sample or measuring solution, 20 sepsis sera were each measured in a fresh state and after storage for 3 days at room temperature. The results are summarized in the table below. They show that the immunoreactivity was virtually unchanged after storage for 3 days. This proven stability of mid-proAM is a major advantage in terms of handling aspects for diagnosis.

TABLE 1

| Patient # | mid-proAM [nmol/l] Day = 0 | mid-proAM [nmol/l] Day = 3 | Change |
|---|---|---|---|
| 1 | 6.2 | 6.1 | 98.8% |
| 2 | 3.3 | 3.2 | 98.1% |
| 3 | 2.2 | 2.1 | 97.0% |
| 4 | 1.6 | 1.5 | 95.4% |
| 5 | 1.1 | 1.0 | 92.7% |
| 6 | 1.3 | 1.2 | 95.7% |
| 7 | 1.9 | 2.1 | 109.6% |
| 8 | 2.6 | 2.7 | 102.8% |
| 9 | 2.8 | 2.7 | 96.4% |
| 10 | 3.1 | 3.1 | 99.9% |
| 11 | 4.6 | 4.9 | 106.3% |
| 12 | 5.8 | 5.9 | 102.1% |
| 13 | 3.6 | 3.4 | 95.2% |
| 14 | 4.2 | 4.6 | 110.7% |
| 15 | 3.0 | 2.4 | 80.0% |
| 16 | 1.2 | 1.3 | 105.5% |
| 17 | 1.5 | 1.5 | 102.2% |
| 18 | 1.7 | 1.8 | 103.4% |
| 19 | 2.0 | 1.8 | 89.5% |
| 20 | 2.1 | 2.0 | 94.1% |

Mean value = 98.8%

In summary, it may be stated that a determination of mid-proAM, for example using an SPCD19 antibody, has numerous advantages over a determination of, for example, AM:

A determination of mid-proAM is not subject to any known restrictions owing to the existence of a binding protein, of fragmentation and of weak concentration dynamics.

The analyte mid-proAM furthermore has good stability, i.e. very little loss of immunoreactivity during storage at room temperature, which is a major practical advantage for diagnostic routine determinations.

Extremely advantageous dynamics are observed, and it is not to be assumed that this is specific for sepsis.

It is therefore to be assumed that a measurement of mid-proAM can have advantages generally for all clinical pictures for which AM concentration increases are described, a determination in sepsis, cardiac and cancer diagnosis appearing particularly advantageous at present.

The invention claimed is:

1. A method for detecting and quantitating in a biological fluid sample from a human the mid-regional partial peptide of proadrenomedullin (mid-proAM) which consists of the sequence of SEQ ID NO: 3, comprising
   (a) contacting the sample with a labeled monoclonal or polyclonal antibody which specifically binds to said mid-proAM partial peptide, and
   (b) detecting and quantitating the resulting peptide:antibody complex using an immunoassay, wherein said immunoassay
      (i) is not a radioimmunoassay, and
      (ii) has a limit of detection of about 50 pmol/l; and
   wherein said immunoassay using said at least one labeled antibody is a sandwich assay further employing at least one additional antibody which specifically binds to a different partial sequence of mid-proAM (SEQ ID NO: 3) from that bound by said at least one labeled antibody; and wherein for said sandwich assay, one of the antibodies is obtained by immunization of an animal with an antigen which contains a synthetic peptide sequence which consists of amino acids 69-86 of pre-proAM (SEQ ID NO: 4), and the other of the antibodies is obtained by immunization with an antigen which contains a synthetic peptide sequence which consists of amino acids 83-94 of pre-proAM (SEQ ID NO: 5).

2. An immunoassay method for detecting and quantitating in a biological fluid sample the mid-regional partial peptide of proadrenomedullin (mid-proAM) which consists of the sequence of SEQ ID NO: 3, comprising contacting the sample with at least one labeled monoclonal or polyclonal antibody which specifically binds to said mid-proAM partial peptide, and detecting the thus-formed antibody:mid-proAM complex,
   wherein said immunoassay
      (a) is not a radioimmunoassay, and
      (b) has a limit of detection of about 50 pmol/l;
   said immunoassay being a sandwich assay further employing at least one additional antibody which specifically binds to a different partial sequence of mid-proAM (SEQ ID NO: 3) from that bound by said at least one labeled antibody; and wherein for said sandwich assay, one of the antibodies is obtained by immunization of an animal with an antigen which contains a synthetic peptide sequence which consists of amino acids 69-86 of pre-proAM (SEQ ID NO: 4), and the other of the antibodies is obtained by immunization with an antigen which contains a synthetic peptide sequence which consists of amino acids 83-94 of pre-proAM (SEQ ID NO: 5).

* * * * *

UNITED STATES PATENT AND TRADEMARK OFFICE
CERTIFICATE OF CORRECTION

PATENT NO. : 9,885,709 B2
APPLICATION NO. : 10/551298
DATED : February 6, 2018
INVENTOR(S) : Andreas Bergmann and Joachim Struck It is certified that error appears in the above-identified patent and that said Letters Patent is hereby corrected as shown below:

On the Title Page

(73) Assignee: reads "B.R.A.H.M.S. GMBH, Henningsdorf, Greece" should read --B.R.A.H.M.S. GMBH, Henningsdorf, Germany--.

Signed and Sealed this
Twelfth Day of June, 2018

Andrei Iancu
*Director of the United States Patent and Trademark Office*

SEQUENCE LISTING

<160> NUMBER OF SEQ ID NOS: 5

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
 1               5                  10                  15

Leu Gly Ala Asp Thr Ala Arg Leu Asp Val Ala Ser Glu Phe Arg Lys
                20                  25                  30

Lys Trp Asn Lys Trp Ala Leu Ser Arg Gly Lys Arg Glu Leu Arg Met
            35                  40                  45

Ser Ser Ser Tyr Pro Thr Gly Leu Ala Asp Val Lys Ala Gly Pro Ala
        50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 52
<212> TYPE: PRT
<213> ORGANISM: Homo sapiens

<400> SEQUENCE: 2

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
    50

<210> SEQ ID NO 3
<211> LENGTH: 48
<212> TYPE: PRT
<213> ORGANISM: Homo sapiens

<400> SEQUENCE: 3

Glu Leu Arg Met Ser Ser Ser Tyr Pro Thr Gly Leu Ala Asp Val Lys
 1               5                  10                  15

Ala Gly Pro Ala Gln Thr Leu Ile Arg Pro Gln Asp Met Lys Gly Ala
                20                  25                  30

```
Ser Arg Ser Pro Glu Asp Ser Ser Pro Asp Ala Ala Arg Ile Arg Val
        35                  40                  45

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Cys Arg Pro Gln Asp Met Lys Gly Ala Ser Arg Ser Pro Glu Asp Ser
 1               5                  10                  15

Ser Pro Asp

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Cys Ser Ser Pro Asp Ala Ala Arg Ile Arg Val Lys Arg
 1               5                  10
```